(12) United States Patent
McKay (10) Patent No.: US 8,597,192 B2
(45) Date of Patent: Dec. 3, 2013

(54) ULTRASONIC DEVICES AND METHODS TO DIAGNOSE PAIN GENERATORS

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 435 days.

(21) Appl. No.: 12/609,198

(22) Filed: Oct. 30, 2009

(65) Prior Publication Data

US 2011/0105905 A1    May 5, 2011

(51) Int. Cl.
*A61B 8/00*    (2006.01)

(52) U.S. Cl.
USPC .......................................................... 600/453

(58) Field of Classification Search
USPC ......... 601/2, 3; 600/407–471; 367/7, 11, 130; 73/625, 626; 128/916
See application file for complete search history.

(56) References Cited

U.S. PATENT DOCUMENTS

| | | | |
|---|---|---|---|
| 4,624,255 A | 11/1986 | Schenck et al. | |
| 4,863,457 A | 9/1989 | Lee | |
| 5,522,844 A | 6/1996 | Johnson | |
| 5,868,789 A | 2/1999 | Huebner | |
| 5,976,105 A | 11/1999 | Marcove et al. | |
| 6,069,129 A | 5/2000 | Sandberg et al. | |
| 6,179,862 B1 | 1/2001 | Sawhney | |
| 6,287,588 B1 | 9/2001 | Shih et al. | |
| 6,328,694 B1 * | 12/2001 | Michaeli | 600/438 |
| 6,331,311 B1 | 12/2001 | Brodbeck et al. | |
| 6,390,982 B1 * | 5/2002 | Bova et al. | 600/443 |
| 6,428,804 B1 | 8/2002 | Suzuki et al. | |
| 6,432,063 B1 | 8/2002 | Marcus | |
| 6,461,631 B1 | 10/2002 | Dunn et al. | |
| 6,491,651 B1 | 12/2002 | Leahy et al. | |
| 6,589,549 B2 | 7/2003 | Shih et al. | |
| 6,630,155 B1 | 10/2003 | Chandrashekar et al. | |
| 6,632,457 B1 | 10/2003 | Sawhney | |
| 6,736,835 B2 | 5/2004 | Pellegrino et al. | |
| 6,756,058 B2 | 6/2004 | Brubaker et al. | |
| 6,773,714 B2 | 8/2004 | Dunn et al. | |
| 6,974,462 B2 | 12/2005 | Sater | |
| 7,144,412 B2 | 12/2006 | Wolf et al. | |
| 7,166,570 B2 | 1/2007 | Hunter et al. | |
| 7,220,281 B2 | 5/2007 | Lambrecht et al. | |
| 7,229,441 B2 | 6/2007 | Trieu et al. | |
| 7,235,043 B2 | 6/2007 | Gellman et al. | |
| 7,318,840 B2 | 1/2008 | McKay | |
| 7,329,259 B2 | 2/2008 | Cragg | |
| 7,361,168 B2 | 4/2008 | Makower et al. | |

(Continued)

FOREIGN PATENT DOCUMENTS

WO    03005961 A2    1/2003

OTHER PUBLICATIONS

Smith, Globe Staff, The Boston Globe, entitled "Most Surgery in Wrong Spot Done on Spine", Jul. 2008.

(Continued)

*Primary Examiner* — Elmer Chao
(74) *Attorney, Agent, or Firm* — Sorell Lenna & Schmidt LLP (57) ABSTRACT

Ultrasonic devices and methods are provided that diagnose one or more pain generators. In some embodiments, the ultrasonic devices and methods are utilized to map one or more pain generators at or near the spine so that appropriate diagnostic and treatment methods can be performed.

5 Claims, 4 Drawing Sheets

(56) References Cited

U.S. PATENT DOCUMENTS

| | | |
|---|---|---|
| 7,367,978 B2 | 5/2008 | Drewry et al. |
| 7,449,019 B2 | 11/2008 | Uchida et al. |
| 7,462,155 B2 | 12/2008 | England |
| 7,482,174 B2 | 1/2009 | Kiefer et al. |
| 2002/0009454 A1 | 1/2002 | Boone et al. |
| 2002/0090398 A1 | 7/2002 | Dunn et al. |
| 2002/0095087 A1* | 7/2002 | Mourad et al. ............ 600/442 |
| 2003/0009153 A1* | 1/2003 | Brisken et al. .......... 604/890.1 |
| 2003/0023257 A1* | 1/2003 | Ishikawa et al. ............ 606/169 |
| 2003/0204191 A1 | 10/2003 | Sater et al. |
| 2004/0072799 A1 | 4/2004 | Li et al. |
| 2004/0082540 A1 | 4/2004 | Hermida Ochoa |
| 2004/0162571 A1* | 8/2004 | Rabiner et al. ............ 606/159 |
| 2004/0214793 A1 | 10/2004 | Hermida Ochoa |
| 2005/0142163 A1 | 6/2005 | Hunter et al. |
| 2005/0186261 A1 | 8/2005 | Avelar et al. |
| 2005/0197293 A1 | 9/2005 | Mellis et al. |
| 2005/0240126 A1 | 10/2005 | Foley et al. |
| 2006/0079773 A1 | 4/2006 | Mourad et al. |
| 2006/0100547 A1 | 5/2006 | Rabiner et al. |
| 2006/0106361 A1 | 5/2006 | Muni et al. |
| 2006/0148903 A1 | 7/2006 | Burch et al. |
| 2006/0184069 A1 | 8/2006 | Vaitekunas |
| 2006/0189944 A1 | 8/2006 | Campbell et al. |
| 2007/0185367 A1 | 8/2007 | Abdou |
| 2007/0243225 A1 | 10/2007 | McKay |
| 2007/0243228 A1 | 10/2007 | McKay |
| 2007/0287934 A1 | 12/2007 | Babaev |
| 2008/0008988 A1 | 1/2008 | McKay et al. |
| 2008/0019969 A1 | 1/2008 | Gorman |
| 2008/0019970 A1 | 1/2008 | Gorman |
| 2008/0019975 A1 | 1/2008 | Gorman |
| 2008/0091207 A1 | 4/2008 | Truckai et al. |
| 2008/0175911 A1 | 7/2008 | McKay et al. |
| 2008/0213283 A1 | 9/2008 | Olmarker et al. |
| 2008/0294261 A1 | 11/2008 | Pauza et al. |
| 2008/0300591 A1 | 12/2008 | Darian et al. |
| 2008/0317805 A1 | 12/2008 | McKay et al. |
| 2009/0024135 A1 | 1/2009 | Triplett et al. |
| 2009/0130019 A1 | 5/2009 | Tobinick |
| 2009/0155199 A1 | 6/2009 | Babaev |
| 2009/0216159 A1 | 8/2009 | Slayton et al. |
| 2009/0254008 A1 | 10/2009 | Shields, Jr. |

OTHER PUBLICATIONS

Zachary et al., In Search of the Elusive Lumbar Spine Pain Generator (website visited Feb. 2009).

U.S. Appl. No. 12/397,422 filed Mar. 4, 2009.

* cited by examiner

ULTRASONIC DEVICES AND METHODS TO DIAGNOSE PAIN GENERATORS

BACKGROUND

Pain can adversely affect patients in many different ways. It can keep the patient from being active, sleeping well, enjoying family and friends, and from eating. Pain can make the patient feel afraid or depressed and prevent full participation in general rehabilitation programs and may even slow recovery.

Pain serves the important biological function of signaling the presence of damage or disease within the body and is often accompanied by inflammation (redness, swelling, and/or burning). There are two categories of pain: acute pain and neuropathic pain. Acute pain refers to pain experienced when tissue is being damaged or is damaged. Acute pain serves at least two physiologically advantageous purposes. First, it warns of dangerous environmental stimuli (such as hot or sharp objects) by triggering reflexive responses that end contact with the dangerous stimuli. Second, if reflexive responses do not avoid dangerous environmental stimuli effectively, or tissue injury or infection otherwise results, acute pain facilitates recuperative behaviors. For example, acute pain associated with an injury or infection encourages an organism to protect the compromised area from further insult or use while the injury or infection heals. Once the dangerous environmental stimulus is removed, or the injury or infection has resolved, acute pain, having served its physiological purpose, ends. As contrasted to acute pain, in general, neuropathic pain serves no beneficial purpose. Neuropathic pain results when pain associated with an injury or infection continues in an area once the injury or infection has resolved.

There are many painful diseases or conditions that require proper pain and/or inflammation control, including but not limited to a spinal disc herniation (i.e., sciatica), lower back pain, lower extremity pain, upper extremity pain, cancer, tissue pain and pain associated with injury or repair of cervical, thoracic, and/or lumbar vertebrae or intervertebral discs, tendons, ligaments, muscles, spondilothesis, stenosis, discogenic back pain, or the like.

Many of the above condition require surgical treatment to try to alleviate or control the pain. For example, an intervertebral disc herniation is a painful condition that may occur in any of the 33 discs of the spine but herniations in the lumbar and the cervical spine are most common. Disc herniations in the cervical spine may cause radiating pain and muscle dysfunction in the arm, which is generally referred to as cervical rhizopathy. While disc herniations in the lumbar spine may induce radiating pain and muscle dysfunction in the leg, which is generally referred to as sciatica. Treatments for intervertebral disc herniations include open or mini-open surgery, using very small opening incisions or percutaneously, utilizing specially designed instruments and radiographic techniques to target the pain generator or area that is involved in the painful condition.

Unfortunately, particularly with pain generators in the spine, the cause for the pain may be difficult to diagnose, as there are numerous structures containing nociceptors and often the pain radiates throughout the body. To complicate matters for the practitioner, the vertebrae of the spine look very similar and are often no more than an inch tall with only a small separation between their bony structures. Sometimes, particularly when the spine is injured or abnormal, it may be difficult to locate the injured or abnormal vertebrae involved in causing the pain. Often times the practitioner will take additional steps such as taking several X-rays, MRIs, CAT scans, and counting the number of vertebrae to ensure the right vertebra is being treated. To diagnose a pain generator from a spinal disc, for example, the practitioner may perform an invasive discography, where a needle is inserted into a disc puncturing the annulus of the disc which may increase incidence of disc degeneration.

In spite of these additional steps, sometimes the wrong vertebra is indeed treated, which subjects the patient to additional surgeries. Other times, the test to diagnose the pain generator itself may increase the risk of disc degeneration. The patient will often feel afraid or depressed and this may prevent full participation in general rehabilitation programs and may even slow recovery. Thus, there is a need to improve the diagnosis of painful spinal diseases. There is also a need to reduce surgical errors from practitioners operating on the wrong tissue site of the spine.

SUMMARY

Methods and devices are provided to diagnose the presence, location and intensity of one or more pain generators at or near the spine. One advantage of the embodiments provided herein is that by utilizing an ultrasonic probe that vibrates tissue at or near the spine, the practitioner can reproduce the pain signals and properly diagnose the cause and location of the pain generator.

A second advantage of the embodiments provided herein is that by positioning an ultrasonic probe that vibrates tissue at or near the spine, the practitioner can reproduce the pain signals and produce a pain map that locates the pain generators so that the practitioner can rule out referred pain that is where the pain sensation is localized to an area completely unrelated to the site of injury. A third advantage is that the disc tissue is not penetrated leading to accelerated disc degeneration. A fourth advantage of the embodiments provided herein is that by properly locating the pain generators, this can dictate the location of the surgery and reduce the risk that the practitioner operates on the wrong area of the patient.

The pain generator may be due to conditions involving pain and/or inflammation. The pain and/or inflammation may for example be due to chronic conditions including, a spinal disc herniation (e.g., sciatica), lower back pain, discogenic back pain, lower extremity pain, upper extremity pain, tissue pain and pain associated with injury or repair of cervical, thoracic, and/or lumbar vertebrae or intervertebral discs, spondilothesis, stenosis or the like.

In one embodiment, an ultrasonic device is provided for diagnosing a pain generator or a suspected pain generator at or near the spine in a patient suffering from pain, the ultrasonic device comprising an ultrasonic probe having a proximal end, a distal end, and a longitudinal axis therebetween, the ultrasonic probe configured to be moved at or near the pain generator or suspected pain generator; an ultrasonic energy source that supplies the ultrasonic probe with an ultrasonic energy; and a transducer for engaging the ultrasonic energy source and the proximal end of the ultrasonic probe to transfer the ultrasonic energy from the ultrasonic energy source along the longitudinal axis to the distal end of the ultrasonic probe, the ultrasonic energy having an intensity to deliver ultrasound energy and produce a pain signal at the pain generator or suspected pain generator.

In a second embodiment, the ultrasonic probe is repositioned and activated at a plurality of suspected pain generators before it is repositioned and activated at a plurality of pain generators so that the location of the pain generators can be mapped.

In another embodiment, a method is provided for diagnosing a location of a pain generator or a suspected pain generator at or near the spine in a patient suffering from pain, the method comprising: positioning an ultrasonic probe at or near the pain generator or suspected pain generator, the ultrasonic probe having a proximal end, a distal end and a longitudinal axis therebetween, the ultrasonic probe supplied with ultrasonic energy from an ultrasonic energy source that transfers ultrasonic energy from a transducer to the proximal end of the ultrasonic probe along the longitudinal axis to the distal end of the ultrasonic probe; and delivering sufficient ultrasonic energy from the distal end of the ultrasonic probe to tissue at or near the pain generator or suspected pain generator to produce a pain signal so as to diagnose the location of the pain generator or suspected pain generator.

In yet another embodiment, a method is provided for diagnosing a pain generator at or near the spine in a patient suffering from pain, the method comprising: positioning an ultrasonic probe at a target tissue site at or near the spine, the ultrasonic probe having a proximal end, a distal end and a longitudinal axis therebetween, the ultrasonic probe supplied with ultrasonic energy from an ultrasonic energy source that transfers ultrasonic energy from a transducer to the proximal end of the ultrasonic probe along the longitudinal axis to the distal end of the ultrasonic probe; delivering a first dose of ultrasonic energy from the distal end of the ultrasonic probe to the target tissue site at or near the spine to produce a first pain signal; re-positioning the ultrasonic probe at a second target tissue site at or near the spine; delivering a second dose of ultrasonic energy from the distal end of the ultrasonic probe to the second target tissue site at or near the spine to produce a second pain signal; and comparing the first dose and the first pain signal to the second dose and the second pain signal to diagnose the pain generator or suspected pain generator, wherein a greater pain signal indicates the presence of the pain generator or a lower pain signal or no pain signal indicates that no pain generator is present or that the ultrasonic probe is positioned further away from the pain generator.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings where:

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings below are not meant to limit the disclosure in any way; embodiments under any one heading may be used in conjunction with embodiments under any other heading.

Definitions

It is noted that, as used in this specification and the appended claims, the singular forms "a," "an," and "the," include plural referents unless expressly and unequivocally limited to one referent. Thus, for example, reference to "a pain regenerator" includes one, two, three or more pain generators.

The term "diagnostic" or "diagnosing" means identifying the presence, absence, and/or location of one or more pain generators or suspected pain generators associated with the pain.

The term "at or near" is intended to include a region extending up to and including from 0 cm to 5 cm from the target tissue site at or near the spine (e.g., nerve, muscle, ligament, bone, vertebra, etc.), as well as interior regions within the target tissue site.

The term "spine" includes neuronal, bony, vascular and soft tissue components. This includes the vertebral bodies and their associated joints (facets, costovertebral joints, or disc interfaces), the intervertebral discs, the intrinsic musculature, the spinal cord, spinal nerves, sympathetic nerves or ganglia associated with the axial skeleton, vertebral or disc innervations, and/or associated blood vessels.

The term "axial" refers to the head, neck and/or back of a patient.

The term "disc" may be one or more discs within a spinal column, including cervical, thoracic or lumbar discs.

The term "disc region" is intended to include a region extending about 5 cm from the surface of a disc, the surface of the disc, as well as interior regions within the disc.

The term "degeneration" refers to anatomical signs of degeneration, which can include changes in the height of the disc, the level of hydration of the disc, ruptured or contained herniation, annular bulging, and the presence of tearing or osteophytes. A reduction in the height of the disc may be one of the most common, early and easily detectable changes present in a degenerating disc. Another sign of degeneration is normally the loss of the T2 weighted signal on an MRI scan; this is indicative of a loss of hydration of the nuclear tissue. The degeneration can be a contained disc that occupies the space determined by the size of the endplates or a herniated disc. Herniation could be of a contained nature called, for example, bulging of the disc or a herniated disc can also be ruptured with release of discal elements, such as the nucleus pulposus, outside the disc. Signs of degeneration such as inflammation, tissue density, changes in pH, increased innervation and vascularization can also be found adjacent to the disc.

The term "radiculopathy" refers to radicular leg or arm pain derived from abnormalities of the disc or elements adjacent to the disc that can affect a spinal root or other neuronal elements within the spinal column.

The term "degeneration" refers to a traumatic or progressive abnormality linked to the development of an axial pain with and without radiculopathy condition. Suitable non-limiting examples of degeneration in the intervertebral disc or the area adjacent to the disc include bulging or protrusion, inflammation, pressure, changes in neuronal, vascular, immune or matrix elements, electrical activity, water content, tissue density, and pH.

The term "pain" includes nociception and the sensation of pain, both of which can be assessed objectively and subjectively, using pain scores and other methods well-known in the art. A person of ordinary skill in the art will recognize that the threshold for pain may vary between different patients. Accordingly, the results of the diagnosing the pain generator or suspected pain generator or the testing and/or monitoring of the pain generator or suspected pain generator may be correlated with the pain measurements according to techniques of pain assessment known in the art. Such correlation enables the practitioner to choose the course of treatment which better fits the needs of the patient. The techniques of pain assessment include, without limitation, VAS, Oswestri, and SF-36 Questionnaires, pain scores from 0 to 10,where 0 is none and 10 is most. These can be used to determine if a pain signal is produced. A "pain signal" includes the patient's perception of pain in response to the tissue having contact with ultrasonic energy. This pain signal can be induced by vibrating the tissue with ultrasonic energy.

Pain, as used herein, also includes allodynia (i.e., increased response to a normally non-noxious stimulus) and hyperalgesia (i.e., increased response to a normally noxious or unpleasant stimulus), which can in turn, be thermal or mechanical (tactile) in nature. In some embodiments, pain is characterized by thermal sensitivity, mechanical sensitivity and/or resting pain. In other embodiments, pain comprises mechanically-induced pain or resting pain. In still other embodiments, the pain comprises resting pain. The pain can be primary or secondary pain, as is well-known in the art. Exemplary types of pain that can be diagnosed and treated by the methods and devices of the present application include, without limitation, back pain in the lumbar regions (low back pain) or cervical region (neck pain), leg pain, sciatic pain, radicular pain (experienced in the lower back and leg from lumber pathology, or in the neck and arm from cervical pathology), or neuropathic pain of the arm, neck, back, lower back, leg, or related pain distributions resulting from disc or spine pathology. As used herein, "neuropathic pain" includes pain arising from injury to the nerve root, dorsal root ganglion or peripheral nerve.

The term "pain generator" refers to the source or cause involved in the painful condition. The term "suspected pain generator" includes the source or cause believed to be involved in the painful condition, yet no definitive diagnosis of the location of the pain generator has been made. Pain generators can occur from, for example, vertebral abnormalities, such as, compression fractures, pars defects, vertebral instability, soft tissue abnormalities in ligaments, tendons, annulus, muscles, cartilaginous structures, joints (e.g., facet joints, intervertebral discs, sacroiliac joints, etc.) or abnormalities resulting from tumors, infection or other infiltrative processes. Pain generators can result from nerve ingrowth into annulus tears and facet capsules, nerve root lesions (e.g., compressive lesions from adjacent discs, hypertrophic facet joints, facet joints cysts, faulty hardware positioning, bony foraminal encroachment, spondylolisthesis, spondylolysis, congenitally short pedicles, nerve sheath tumors, granulation tissue and/or arachnoiditis, etc.), spinal nerve compression (e.g., spinal stenosis), peripheral nerve lesions, femoral neuropathy, meralgia paresthetica, peroneal neuropathy, asymmetrical neuropathies, lower limb joint pathology, vascular pathology, degenerative disc and joint disease or the like. In some embodiments, the methods and devices provided can be used to locate the pain generator that causes persistent pain and/or radicular pain, which accompany underlying spinal abnormalities. The term "no pain generator" includes tissue that does not contain any pain generator.

The term "surgical procedure" includes a procedure in which one or more incisions are made into the body in order to repair damage or remove diseased tissue. In some embodiments, the surgical procedure can include implanting one or more drug depots or other implantable device.

The term "spinal surgery" includes a procedure in which one or more incisions are made and requires manipulation of spinal tissues, with or without removal and/or repair of spinal tissues. Examples of spinal surgery include, but are not limited to, repair of a herniated disc, adhesioloysis, radiofrequency neurotomy; intradiscal electrothermal therapy, fusion of vertebrae, full or partial discectomy, laminectomy, laminotomy, or laminoplasty, or the like.

The term "probe" includes a device capable of propagating an energy emitted by the ultrasonic energy source along a longitudinal axis of the probe, resolving the energy into a target tissue site to cause mechanical movement if the tissue.

The term "practitioner" means a person who is using the methods and/or devices of the current disclosure on the patient. This term includes, without limitation, doctors (e.g., surgeons, interventional specialists, physicians), nurses, nurse practitioners, other medical personnel, clinicians, veterinarians, or scientists.

The drug depot can comprise an analgesic or an anti-inflammatory agent. The phrase "anti-inflammatory agent" refers to an agent or compound that has anti-inflammatory effects. These agents may remedy pain by reducing inflammation. Anti-inflammatory agents also include those agents in a different classification with anti-inflammatory properties, such as, for example, amitriptyline, carbamazepine, gabapentin, pregabalin, clonidine, or other alpha adrenergic receptor agonist or a combination thereof.

The pain and/or inflammation may for example be due to chronic conditions including rheumatoid arthritis, osteoarthritis, a spinal disc herniation (e.g., sciatica), carpal/tarsal tunnel syndrome, lower back pain, discogenic back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, spondilothesis, stenosis, or joint pain or the like.

A "drug depot" is the composition in which at least one anti-inflammatory agent and/or at least one analgesic agent or the pharmaceutically acceptable salts of either or both are administered to the body. Thus, a drug depot may comprise a physical structure to facilitate implantation and retention in a desired site (e.g., a disc space, a spinal canal, a tissue of the patient, particularly at or near a site of surgery, pain, or site of inflammation, etc.). The drug depot also comprises the drug itself. The term "drug" as used herein is generally meant to refer to any substance that alters the physiology of a patient. The term "drug" may be used interchangeably herein with the terms "therapeutic agent," "therapeutically effective amount," and "active pharmaceutical ingredient" or "API." It will be understood that unless otherwise specified a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 0.1 cm to about 5 cm from the implant site, and comprises at least one anti-inflammatory agent or its pharmaceutically acceptable salt and/or at least one analgesic agent or its pharmaceutically acceptable salt.

A "depot" includes but is not limited to capsules, microspheres, microparticles, microcapsules, microfibers particles, nanospheres, nanoparticles, coating, matrices, wafers, pills, pellets, emulsions, liposomes, micelles, gels, or other pharmaceutical delivery compositions or a combination thereof. In some embodiments, the depot can include a pump. Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof.

A "therapeutically effective amount" or "effective amount" is such that when administered, the drug results in alteration of the biological activity, such as, for example, inhibition of inflammation, reduction or alleviation of pain, improvement in the condition, etc. The dosage administered to a patient can unless otherwise specified or apparent from context be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments the drug depot formulation is designed for immediate release. In other embodiments the drug depot formulation is designed for sustained release. In other embodiments, the drug depot formulation comprises one or more immediate release surfaces and one or more sustain release surfaces.

The term "mammal" refers to organisms from the taxonomy class "mammalian," including but not limited to humans, other primates such as chimpanzees, apes, orangutans and monkeys, rats, mice, cats, dogs, cows, horses, etc. In various embodiments, the mammal is a human patient.

The term "implantable" as utilized herein refers to a device (e.g., ultrasonic probe, drug depot) retaining potential for successful placement within a mammal.

Treating or treatment of a disease or condition refers to executing a protocol, which may include the use of the ultrasonic device herein and/or administering one or more drugs to a patient (human, normal or otherwise, or other mammal), in an effort to diagnose and alleviate signs or symptoms of the disease. Alleviation can occur prior to signs or symptoms of the disease or condition appearing, as well as after their appearance. Thus, "treating" or "treatment" includes "preventing" or "prevention" of disease or undesirable condition. In addition, "treating" or "treatment" does not require complete alleviation of signs or symptoms, does not require a cure, and specifically includes protocols that have only a marginal effect on the patient. "Reducing pain" includes a decrease in pain and does not require complete alleviation of pain signs or symptoms, and does not require a cure. In various embodiments, reducing pain includes even a marginal decrease in pain. By way of example, the administration of the effective dosages of at least one analgesic agent and/or at least one anti-inflammatory agent may be used to prevent, treat or relieve the symptoms of pain and/or inflammation.

"Localized" delivery includes delivery where ultrasonic energy is directed at the target tissue, for example, a nerve root of the nervous system or a region of the brain, or in close proximity (within about 5 cm, or preferably within about 2 cm, or within about 1 cm, or less for example) thereto. In some embodiments, localized delivery includes also delivering a drug depot locally to the target tissue site.

Ultrasonic Device

In one embodiment, an ultrasonic device is provided for diagnosing a pain generator or a suspected pain generator at or near the spine in a patient suffering from pain, the ultrasonic device comprising an ultrasonic probe having a proximal end, a distal end and a longitudinal axis therebetween, the ultrasonic probe configured to be moved at or near the pain generator or suspected pain generator; an ultrasonic energy source that supplies the ultrasonic probe with an ultrasonic energy; and a transducer for engaging the ultrasonic energy source and the proximal end of the ultrasonic probe to transfer the ultrasonic energy from the ultrasonic energy source along the longitudinal axis to the distal end of the ultrasonic probe, the ultrasonic energy having an intensity to deliver ultrasound energy and produce a pain signal at the pain generator or suspected pain generator.

Figure 1:
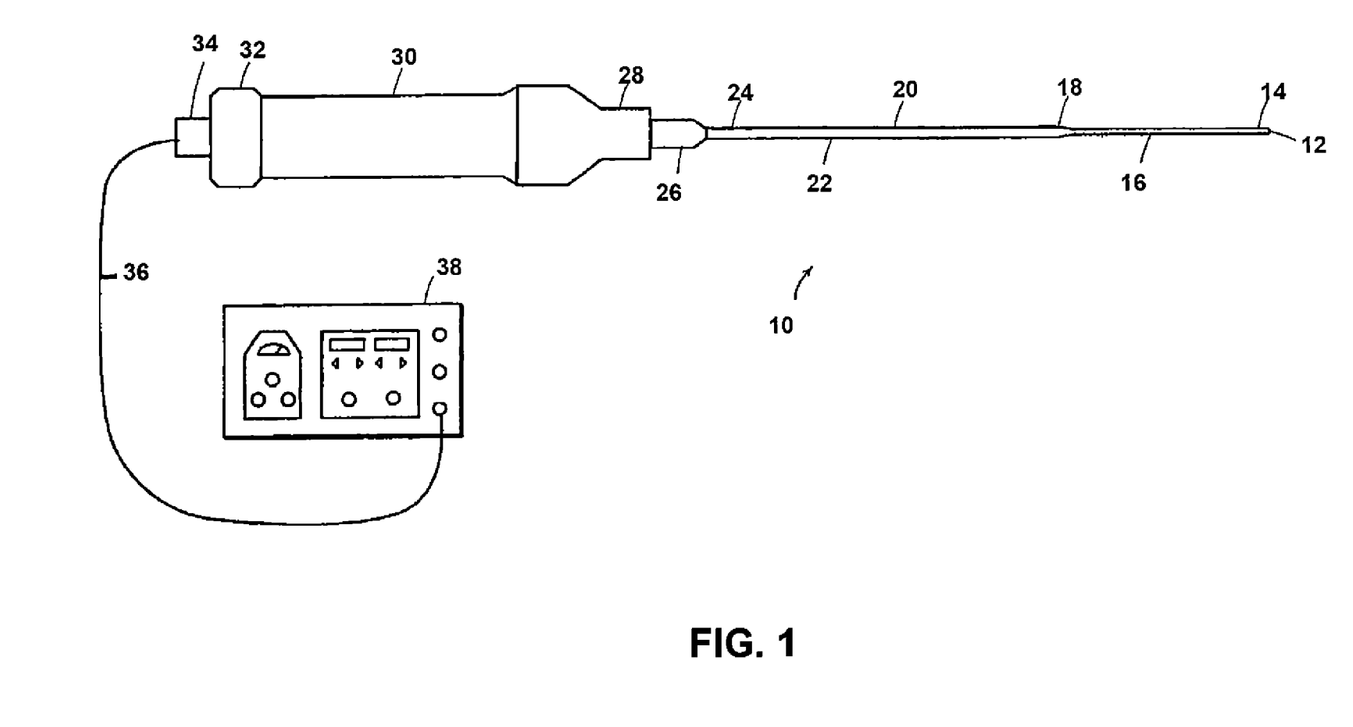
FIG. 1 illustrates a side plan view of an embodiment of an ultrasonic medical device of the present application having a non-uniform transition from a proximal end of the ultrasonic probe to a distal end of the ultrasonic probe.

Referring to FIG. 1, an ultrasonic medical device 10 of the present application is provided that is configured to be moved at or near the pain generator or suspected pain generator and deliver ultrasound energy at the target tissue site to produce a pain signal at or near the pain generator or suspected pain generator. The ultrasonic medical device 10 includes an ultrasonic probe 22 which is coupled to an ultrasonic energy source or generator 38 via connecting wire 36 for the production of an ultrasonic energy. The ultrasonic probe 22 is inserted through the skin to a target tissue site at or near the spine (e.g., at an area comprising at least one muscle, ligament, tendon, cartilage near the spine, or spinal nerve, spinal disc, spinal foraminal space near the spinal nerve root, facet or spinal canal) in a patient suffering from pain, where ultrasonic energy vibrates to the target tissue site and is of an intensity to produce a pain signal.

A handle 30 comprising a proximal end 32 and a distal end 28 surrounds a transducer within the handle 30. The handle may have grips or wings (not shown) that make it easier for the practitioner to manipulate the ultrasonic probe. The transducer, having a proximal end engages the ultrasonic energy source 38 and has a distal end 26 coupled to a proximal end 24 of the ultrasonic probe 22, transmits the ultrasonic energy to the ultrasonic probe 22. A connector 34 and a connecting wire 36 engage the ultrasonic energy source 38 to the transducer. The ultrasonic probe 22 includes the proximal end 24, a distal end 14 that ends in a probe tip 12 and a longitudinal axis between the proximal end 24 and the distal end 14. In an embodiment shown in FIG. 1, a diameter of the ultrasonic probe 22 decreases from a first defined interval 20 to a second defined interval 16 along the longitudinal axis of the ultrasonic probe 22 over a transition 18. One advantage of the embodiments provided herein is that by utilizing an ultrasonic probe that vibrates tissue at or near the spine, the practitioner can reproduce the pain signals and properly diagnose the cause and location of the pain generator. A second advantage of the embodiments provided herein is that positioning an ultrasonic probe that vibrates tissue at or near the spine, the practitioner can reproduce the pain signals and produce a pain map that locates the pain generators so that the practitioner can rule out referred pain that is where the pain sensation is localized to an area completely unrelated to the site of injury.

For example, as spinal discs and facets begin to degenerate, blood vessels and nerve fibers grow into cracks of the annulus, facet capsules, or other anatomic structures. These nerve fibers cause pain during certain movements. Using the ultrasonic medical device of the present application, the ultrasonic probe is positioned at or near a spinal disc or facet. The frequency of the probe is adjusted to mechanically vibrate the surrounding tissue and nerve fibers to induce a localized pain signal. In some embodiments, the ultrasound generated from the device will vibrate newly growing or sprouting nerve fibers and blood vessels that are growing in the body in an attempt to repair damaged tissue. The ultrasonic device and methods will vibrate these areas of new growth that are sensitive and a pain signal will be generated by the patient. The awake patient can notify the practitioner when a pain signal is produced (e.g., when pain is induced). The practitioner notes the location of the pain signal and then repositions the ultrasonic probe to another target tissue site at a pain generator or suspected generator. The frequency of the probe is adjusted to mechanically vibrate the surrounding tissue and nerve fibers to induce a localized pain signal. The awake patient can notify the practitioner when a pain signal is reproduced (e.g., when pain is induced for a second time). The practitioner notes the location of the pain signal and if the lower amount of the ultrasound dose was needed to produce a pain signal. If so, then the practitioner is approaching the pain generator.

Of course, the practitioner will minimize having to reposition the ultrasonic probe. The practitioner will, in some embodiments, first place the probe at the suspected pain generator(s). If a negative response or no pain signal is obtained, then the practitioner will go to subsequent suspected areas of pain generator(s). The practitioner will use the results in a serial or process of elimination fashion. In this way, the practitioner can create a pain generator map and triangulate the one or more pain generators, which will aid in the diagnosis, prognosis and treatment of the spinal disease.

In some embodiments, if the spinal area is damaged and the ultrasonic probe is near the damaged area, a lower amount of ultrasound is needed to vibrate the tissue at or near the damaged area and cause a pain signal. The practitioner would then know he or she is at or near the pain generator. Thus, the first indicator of a pain source is a positive response from the patient, the amount of ultrasound would be an indictor of the severity of the pain source.

The ultrasonic medical device and methods described herein will be helpful for the practitioner to determine if the pain is being generated just from the facets or disc, and the practitioner can decide if a less invasive therapy such as conservative care, an epidural injection, drug depot implantation, posterior stabilization, or fusion is required. It will also provide information whether the pain is localized enough to result in a good clinical outcome or the pain is more diffuse requiring a multi-level spinal surgery.

Figure 2:
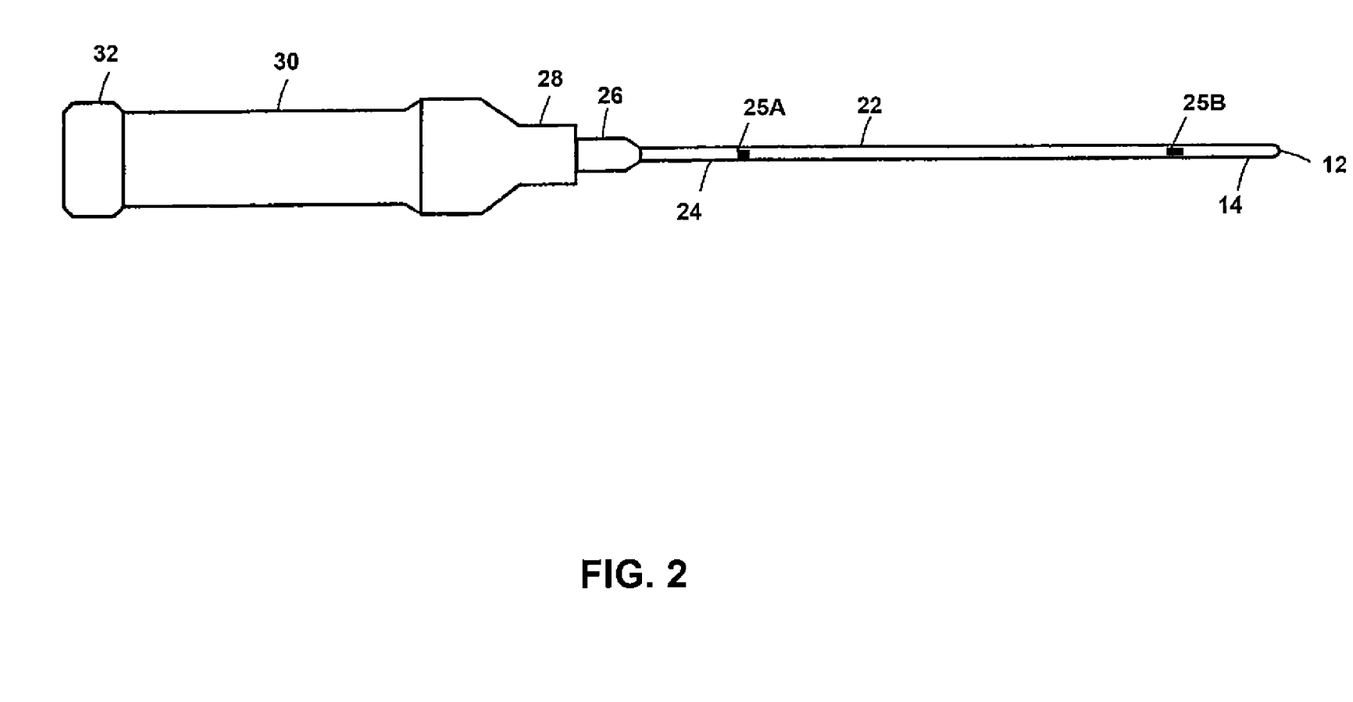
FIG. 2 illustrates a side plan view of an embodiment of an ultrasonic probe of the present application having an approximately uniform diameter from a proximal end of the ultrasonic probe to a distal end of the ultrasonic probe.

In another embodiment of the present application shown in FIG. 2, the diameter of the ultrasonic probe 22 is approximately uniform from the proximal end 24 of the ultrasonic probe 22 to the distal end 14 of the ultrasonic probe 22 having tip 12. A coupling 26 engages the proximal end 24 of the ultrasonic probe 22 to the transducer within the handle 30. A handle 30 comprising a proximal end 32 and a distal end 28 surrounds a transducer within the handle 30. The handle may have grips or wings (not shown) that make it easier for the practitioner to manipulate the ultrasonic probe. The transducer, having a proximal end engages the ultrasonic energy source and has a distal end 26 coupled to a proximal end 24 of the ultrasonic probe 22, transmits the ultrasonic energy to the ultrasonic probe 22. In some embodiments, the coupling 26 is a quick attachment-detachment system. An ultrasonic probe device with a quick attachment-detachment system is described in U.S. Pat. No. 6,695,782 and co-pending patent applications U.S. Ser. Nos. 10/268,487 and 10/268,843,and the entirety of all these patents and patent applications are hereby incorporated herein by reference. In some embodiments, the coupling 26 is threading or reverse threading that can be turned to connect it. In some embodiments, the coupling 26 can be a leur-lock connection.

In some embodiments, the ultrasonic probe 22 is a wire. In some embodiments of the present application, the ultrasonic probe 22 is elongated. In some embodiments of the present application, the diameter of the ultrasonic probe decreases from the first defined interval 20 to the second defined interval 16 (FIG. 1). In some embodiments of the present application, the diameter of the ultrasonic probe 22 decreases at greater than two defined intervals. In some embodiments of the present application, the transitions 18 of the ultrasonic probe 22 are tapered to gradually change the diameter from the proximal end 24 to the distal end 14 along the longitudinal axis of the ultrasonic probe 22. In some embodiments of the present application, the transitions 18 of the ultrasonic probe 22 are stepwise to change the diameter from the proximal end 24 to the distal end 14 along the longitudinal axis of the ultrasonic probe 22. Those skilled in the art will recognize that there can be any number of defined intervals and transitions, and that the transitions can be of any distance and any shape.

In some embodiments of the present application, the gradual change of the diameter from the proximal end 24 to the distal end 14 occurs over the at least one transition 18 with each transition 18 having an approximately equal length. In some embodiments of the present application, the gradual change of the diameter from the proximal end 24 to the distal end 14 occurs over a plurality of transitions 18 with each transition 18 having a varying length. The transition 18 refers to a section where the diameter varies from a first diameter to a second diameter (shown in FIG. 1).

In some embodiments of the present application, the ultrasonic probe 22 has a small diameter. In some embodiment of the present application, the diameter of the ultrasonic probe 22 gradually decreases from the proximal end 24 to the distal end 14. In some embodiments of the present application, the diameter of the distal end 14 of the ultrasonic probe 22 is about 0.004 inches. In some embodiments of the present application, the diameter of the distal end 14 of the ultrasonic probe 22 is about 0.022 inches. In some embodiments of the present application, the diameter of the distal end 14 of the ultrasonic probe 22 varies between about 0.003 inches and about 0.025 inches. Those skilled in the art will recognize an ultrasonic probe 22 can have a diameter at the distal end 14 smaller than about 0.003 inches, larger than about 0.025 inches, and between about 0.003 inches and about 0.025 inches.

In some embodiments of the present application, the diameter of the proximal end 24 of the ultrasonic probe 22 is about 0.012 inches. In some embodiments of the present application, the diameter of the proximal end 24 of the ultrasonic probe 22 is about 0.025 inches. In some embodiments of the present application, the diameter of the proximal end 24 of the ultrasonic probe 22 varies between about 0.003 inches and about 0.025 inches. Those skilled in the art will recognize the ultrasonic probe 22 can have a diameter at the proximal end 24 smaller than about 0.003 inches, larger than about 0.025 inches, and between about 0.003 inches and about 0.025 inches.

In some embodiments, the distal end of the probe comprises a probe tip 12 that can be any shape including, but not limited to, rounded, bent, flat, pointed, smooth, blunt, ball, other shapes, or a combination thereof. The ultrasound probe tip may comprise an orifice or orifices that may deliver a coupling medium such as a liquid flow to the target area. The orifice or orifices may also be used to extract a coupling medium or fluid that is delivered to the target area. The orifice or orifices may be located anywhere on the ultrasound tip. In some embodiments, the tip can directly contact the target tissue site and not use any coupling medium, such as liquid fluid, to contact the target tissue site. In some embodiments the tip of the probe does not have an orifice. In some embodiments, the probe tip 12 may be held flat against the target tissue site to diagnose the pain generator or suspected pain generator during diagnosing or it may be held at an angle. During application of the ultrasonic energy to the tissue, the probe tip 12, or any portion of the probe 22 (24, 20, 18, 16, and/or 14 in FIG. 1, and 24, 14 and 12 in FIG. 2), may be moved latitudinally, moved longitudinally, rotated, lifted, or any combination thereof. If the tip of the probe is rotated during application, then ultrasound energy may be delivered to the external sides of the target tissue area, and the back surface of the target tissue area. If the ultrasound tip is lifted during application of the ultrasonic energy to the tissue, then ultrasound energy may be delivered from both the radial side of the ultrasound tip and the distal end of the ultrasound tip. In some embodiments, depending on the ultrasonic probe, the ultrasound could be transmitted in an axial direction to the probe shaft or at an angle up to perpendicular to the probe shaft.

In some embodiments, the probe tip 12 is smooth to prevent damage to the tissue. In some embodiments of the present application, the ultrasonic energy source 38 is a physical part of the ultrasonic medical device 10. In some embodiments of the present application, the ultrasonic energy source 38 is not a physical part of the ultrasonic medical device 10.

It will be appreciated by those with skill in the art that the probe 22 can be a cannula or needle that can be a part of a ultrasonic medical device 10 e.g., a syringe, a gun delivery device, or any medical device suitable for the application of ultrasound to a targeted tissue, organ or anatomic region. The cannula or needle of the ultrasonic medical device is designed to cause minimal physical and psychological trauma to the patient.

Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style 12 vital for accurate application of ultrasound depending on the anatomic site for implantation. Examples of tip styles include, for example, blunt tips, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the cannula or needle of the ultrasonic probe 22, among other things, will depend on the site for implantation. For example, the width of the epidural space is only about 3-5 mm for the thoracic region and about 5-7 mm for the lumbar region. Thus, the ultrasonic probes having the needle or cannula, in various embodiments, can be designed for these specific areas. In various embodiments, the cannula or needle may be inserted using a transforaminal approach in the spinal foramen space, for example, along an inflamed nerve root and the ultrasound can be applied at this site to determine if there is a pain generator. Typically, the transforaminal approach involves approaching the intervertebral space through the intervertebral foramina.

Some examples of lengths of the cannula or needle of the ultrasonic probe may include, but are not limited to, from about 50 to 150 mm in length, for example, about 65 mm for epidural pediatric use, about 85 mm for a standard adult and about 110 mm for an obese adult patient. The thickness of the cannula or needle will also depend on the site of application of the ultrasound. In various embodiments, the thickness includes, but is not limited to, from about 0.05 to about 1.655. The gauge of the cannula or needle may be the widest or smallest diameter or a diameter in between for insertion into a human or animal body. The widest diameter is typically about 14 gauge, while the smallest diameter is about 25 gauge. In various embodiments the gauge of the needle or cannula is about 18 to about 22 gauge. In some embodiments, the cannula or needle is designed for maximum transmission of ultrasound.

Figure 3:
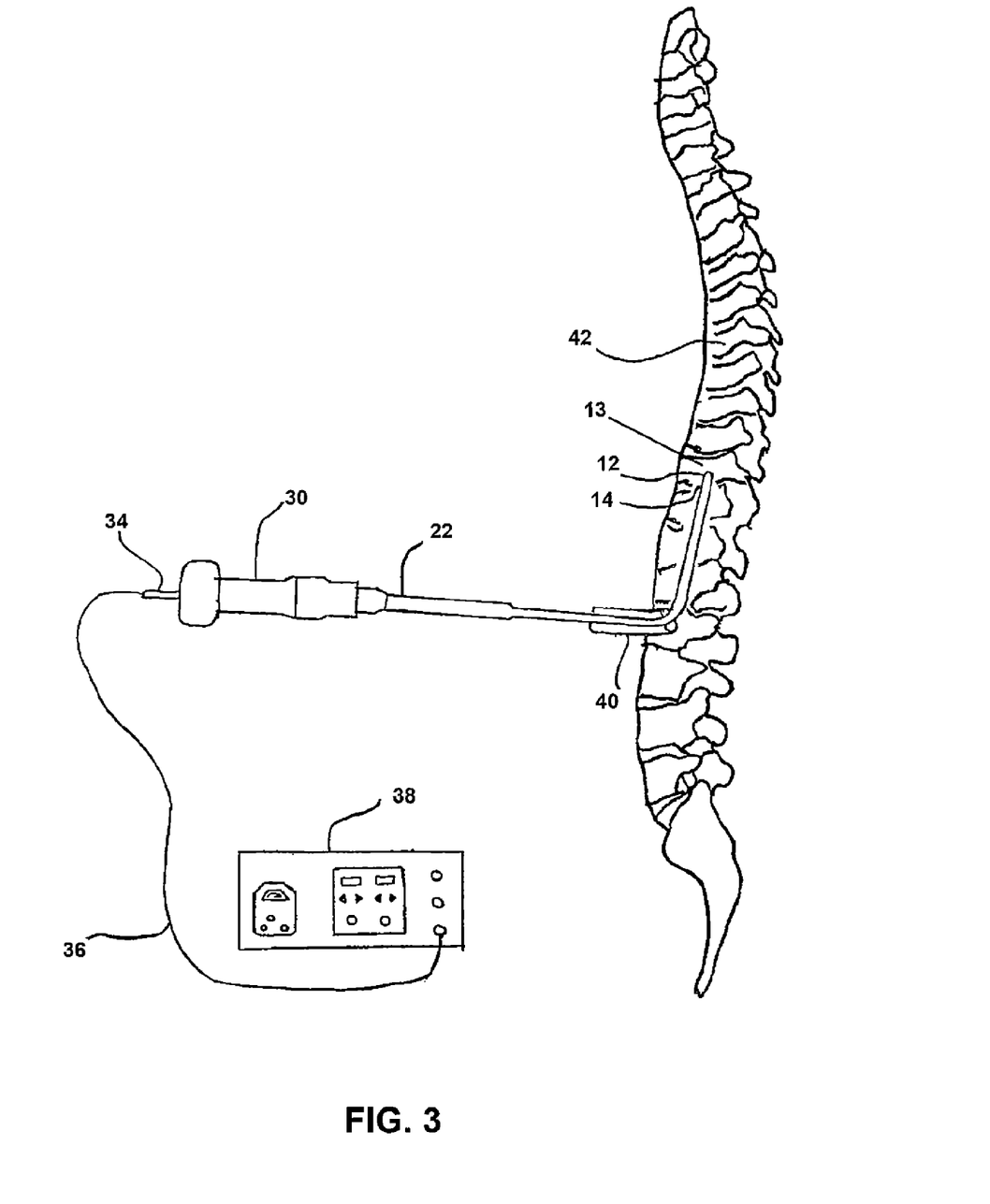
FIG. 3 illustrates a side plan view of an embodiment of the ultrasonic medical device having an introducer to guide the ultrasonic probe to a target tissue site within an area of the spine.

FIG. 3 illustrates a side plan view of the ultrasonic medical device of the present application inserted into the spine 42. The spine 42 comprises a plurality of vertebrae that provide structural support for the spine, and protect and encase the spinal cord. The flexibility of the ultrasonic probe 22 allows the ultrasonic probe 22 to be navigated within the spine 42. In some embodiments, the ultrasonic medical device of the present application is configured to be moved at or near the pain generator or suspected pain generator 13 and deliver ultrasound energy at the target tissue site to produce a pain signal at the pain generator or suspected pain generator and then the patient monitored for pain response. The ultrasonic medical device includes an ultrasonic probe 22 which is coupled to an ultrasonic energy source or generator 38 via connecting wire 36 for the production of an ultrasonic energy. The ultrasonic energy source may be part or coupled to imaging devices used for radiography, fluoroscopy, luminescence, PET, SPECT, CT, MRI, and/or X-ray imaging techniques and display images as the probe is inserted into the spine. The ultrasonic probe 22 is inserted through the skin to a target tissue site at or near the pain generator or suspected pain generator 13 of the spine (e.g., at an area comprising at least one muscle, ligament, tendon, cartilage near the spine, or spinal nerve, spinal disc, spinal foraminal space near the spinal nerve root, facet, annulus, or spinal canal) in a patient suffering from pain, where ultrasonic energy vibrates to the target tissue site of the pain generator or suspected pain generator and is of an intensity to produce a pain signal at or near the target site and then the patient monitored for the pain response.

A handle 30 comprising surrounds a transducer within the handle 30. The handle may have grips or wings (not shown) that make it easier for the practitioner to manipulate the ultrasonic probe. The transducer engages the ultrasonic energy source 38 and has a connector 34 and a connecting wire 36 that engages the ultrasonic energy source 38 to the transducer. The ultrasonic probe 22 includes distal end 14 (shown angled upward) that ends in a probe tip 12 and a longitudinal axis between the tip and the introducer 40. In an embodiment shown in FIG. 3, an introducer 40 is first inserted into the spine, the introducer may be straight or angled and has a channel or elongated shaft to receive at least the distal end of the probe to guide the distal end of the probe 14 and the tip 12 to the target tissue site at or near a suspected pain generator 13. In some embodiments, the introducer can be a catheter, a guide catheter, or a sheath. In some embodiments the ultrasonic probe 22 is flexible. The flexibility of the ultrasonic probe 22 allows the ultrasonic probe 22 to be maneuvered along a bend in the spine. The flexibility of the ultrasonic probe 22 allows the ultrasonic probe 22 to be bent, deflected and flexed through the introducer 40 and moved along the length of the spine 42 to the desired target tissue site. The position of the insertion of the ultrasonic probe 22 relative to the longitudinal axis of the spine 42 is often dictated by anatomical consideration.

In some embodiments, the ultrasonic probe proximal end, distal end, and/or longitudinal axis therebetween and/or the introducer can be retractable or extendible, so that the probe can retract or extend to the target tissue site. In embodiments, where an introducer is used, the ultrasonic probe can retract or extend within the introducer to contact the target tissue site. For example, the ultrasonic probe or at least the distal end of the ultrasonic probe can retract a short distance and then after the introducer penetrates the skin, the ultrasonic probe can extend to contact the target tissue site or the introducer can be retracted so that the ultrasonic probe can contact the target tissue site.

Using the ultrasonic medical device of the present application, the ultrasonic probe is positioned at or near a spinal disc or facet. The frequency of the probe is adjusted to mechanically vibrate the surrounding tissue and nerve fibers to induce a localized pain signal. The awake patient can notify the practitioner when a pain signal is produced (e.g., when pain is induced). The practitioner notes the location of the pain signal and then re-positions the ultrasonic probe to another target tissue site at a pain generator or suspected generator. The frequency of the repositioned probe is adjusted to mechanically vibrate the surrounding tissue and nerve fibers to induce a localized pain signal. The awake patient can notify the practitioner when a pain signal is reproduced (e.g., when pain is induced for a second time). The practitioner notes the location of the pain signal and if the lower amount of the ultrasound dose was needed to produce a pain signal. If so, then the practitioner is approaching the pain generator. Again this is an indicator of the intensity of the pain source. In this way, the practitioner can create a pain generator map and triangulate the one or more pain generators, which will aid in the diagnosis, prognosis and treatment of the spinal disease.

To diagnose a pain generator from a spinal disc, for example, the practitioner may perform an invasive discography, where a needle is inserted into a disc puncturing the annulus of the disc which may increase incidence of disc degeneration. This ultrasonic test has the advantage of not having to puncturing the annulus of a disc.

In some embodiments, where the suspected pain generator is a spinal disc, the ultrasonic probe may be placed just up against the disc, but does not penetrate the disc or facet joint or annulus during the procedure. In some embodiments, the ultrasonic probe may penetrate the disc or facet joint or annulus.

Figure 4:
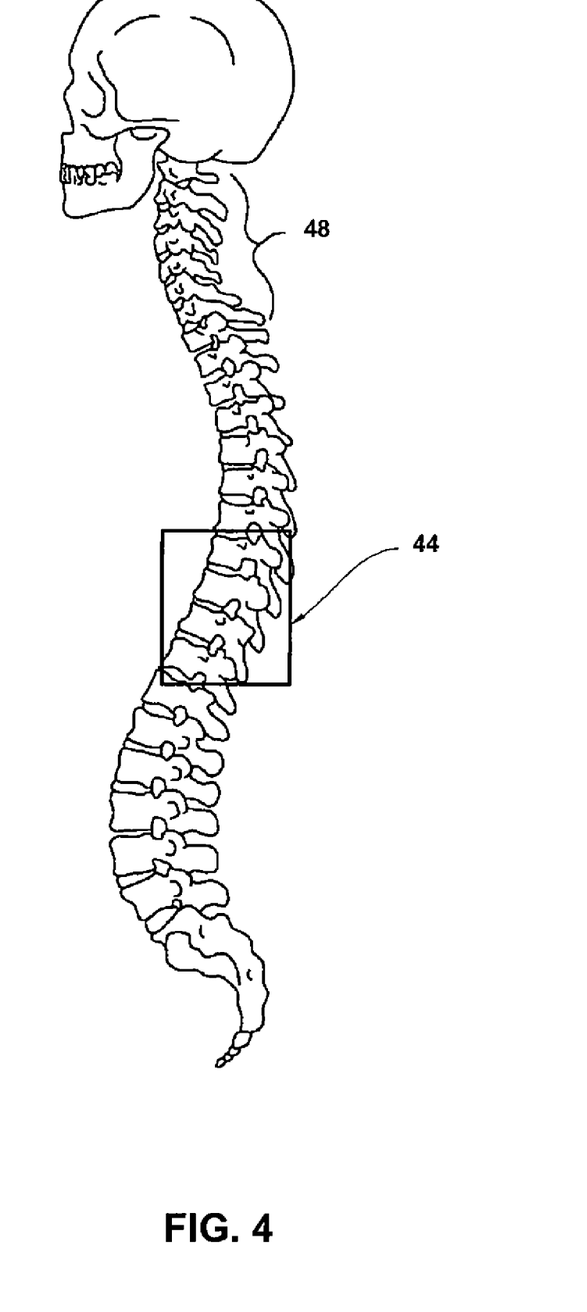
FIG. 4 illustrates a side view of a region of the spine where the pain generators or suspected pain generators can be mapped.

FIG. 4 illustrates a side view of a region of the spine where the pain generators or suspected pain generators can be mapped at section 44. It should be understood by those of ordinary skill in the art that other regions at or near the spine can be mapped for pain generators, such as the upper part of the spine shown as area 48.

In some embodiments, optionally LED sensors can be placed on or in the proximal end (25A in FIG. 2) or distal end of the probe (25B in FIG. 2) or both. These LED sensors can be coupled to overhead cameras (not shown) so the overhead cameras can track the probes position and direction and the position points from the probe's LED sensors can be superimposed onto a 3D CT reconstructed image of the spine on the computer. An example of a suitable system that the ultrasonic probe can be coupled to or used in conjunction with is StealthStation® iNAV (available from Medtronic Sofamor Danek, Memphis, Tenn.) which allows tracking of the target tissue site. In this way, the practitioner will know exactly where he/she is at and the source of pain, when a positive pain response occurs. Thus identifying the position of the pain generator.

Ultrasonic Energy

The ultrasonic probe vibrates the surrounding tissue to induce one or more pain signals. The ultrasonic energy directed to the tissues, vibrates the tissue and does not destroy, ablate or bore holes or bore cavities through the tissues. The dose of the ultrasound energy can be set to be high and low frequencies. In some embodiments, the ultrasound is applied to the target tissue site for 0.5, 0.75, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 55, or 60 seconds or a time sufficient to generate a pain signal. Of course the more damage to the tissue the quicker the time for a pain response. If no pain response within 10 seconds, then the practitioner knows he or she is not near a pain generator.

The intensity of the ultrasound energy can be controlled through a variation in the ultrasound parameters such as the frequency, the amplitude, and the treatment time. The frequency range for the ultrasound energy can be, for example, 15 kHz to 20 MHz. In some embodiments, the low-frequency ultrasound range is 20 kHz-100 kHz, or 25 kHz-50 kHz, or 30 kHz-50 kHz. In some embodiments, the ultrasound energy emitted by the ultrasonic probe can be a high-frequency ultrasound energy in the range of about 0.7 MHz-3 MHz or 0.7

MHz-1.0 MHz. The amplitude of the low-frequency ultrasound energy can be 5 microns and above, with the preferred low-frequency amplitude to be in range of 30 microns to 100 microns, and the recommended low-frequency amplitude value is 100 microns. The amplitude of the high-frequency ultrasound energy can be 1 micron and above, with the preferred high-frequency amplitude to be at least 5 microns, and the recommended high-frequency amplitude value is 10 microns. Thus, the ultrasonic probe can be set to emit the above doses of high and low frequency ultrasound energy. There are a variety of factors that may influence the dosage given to the target tissue site. These factors may include the type of tissue being treated, the condition of the spine, and the size of a spinal defect or location.

In some embodiments, the ultrasonic probe can be set depending on the type of tissue the probe will be placed at or near. For example, the ultrasonic probe can be set to deliver high or low frequency ultrasound depending on the type of tissue the pain generator or suspected pain generator is at or near (e.g., annulus, nucleus, facet capsule, nerve root, etc.).

In some embodiments, a method is provided for diagnosing a location of a pain generator or a suspected pain generator at or near the spine in a patient suffering from pain, the method comprising: positioning an ultrasonic probe at or near the pain generator or suspected pain generator, the ultrasonic probe having a proximal end, a distal end and a longitudinal axis there between, the ultrasonic probe supplied with ultrasonic energy from an ultrasonic energy source that transfers ultrasonic energy from a transducer to the proximal end of the ultrasonic probe along the longitudinal axis to the distal end of the ultrasonic probe; and delivering sufficient ultrasonic energy from the distal end of the ultrasonic probe to tissue at or near the pain generator or suspected pain generator to produce a pain signal so as to diagnose the location of the pain generator or suspected pain generator.

In some embodiments, a method is provided where the ultrasonic probe is re-positioned at a suspected pain generator a plurality of times before it is positioned at a pain generator, so that the location of the pain generator is diagnosed. Of course, the practitioner will try to limit the number of times the ultrasonic probe is repositioned. In some embodiments, a method is provided where the ultrasonic probe is re-positioned at a plurality of suspected pain generators before it is re-positioned at a plurality of pain generators so that the location of the pain generators can be mapped.

In some embodiments, the method involves targeting a target tissue site to determine if one or more pain generators are present. Ultrasonic energy is provided at a first dose to the target tissue site using the ultrasonic probe. If the first dose is sufficient to stimulate pain, the practitioner then notes the location and verifies that the stimulated target tissue is a pain generator and then moves to another location of the pain generator or suspected pain generator. If there is no pain signal (e.g., there is no pain or the scaled pain score is lower), the practitioner can increase the ultrasonic dosage until a pain signal is received. If no pain signal is exhibited by the patient, the practitioner can note that no pain generator was diagnosed and reposition the probe to the another target tissue area. The dose that is applied to the target tissue site can be gradually increased, decreased or remain the same to diagnose the pain generator. Based on the patient's response, for example, if the ultrasound dose is lower and the patient experiences more pain when the probe is placed at the target tissue site, the practitioner notes this and now knows that he/she is getting closer to the pain generator or at the pain generator. The ultrasonic probe can be repositioned and the second target tissue area tested with the same or decreased dose and if the pain signal from the patient is greater (e.g., the scaled pain score is higher), the practitioner notes this and now knows that he/she is getting closer to the pain generator or at the pain generator. Likewise, the ultrasonic probe can be repositioned and the third target tissue area tested with the same or increased dose and if the pain signal from the patient is less, then the practitioner notes this and now knows that he/she is getting farther from the pain generator. This procedure can be repeated a plurality of times. In this way, many focal points of the pain generator and non-pain generator can be mapped and true pain generators can be mapped and diagnosed.

In some embodiments, by using the ultrasonic devices and methods described herein, the practitioner can rule out referred pain—that is where the pain sensation is localized to an area completely unrelated to the site of injury. Thus, the location of the pain generator is undetermined as no definitive diagnosis can be made and the practitioner will now monitor the patient and examine other areas to determine the location of the pain generator. It will be understood by one of ordinary skill in the art that the pain the patient experiences can be assessed objectively and subjectively, using pain scores and other methods well-known in the art.

If the pain generator can not be isolated, the practitioner will perform further physical examinations to determine location of the pain generator. In some embodiments, the practitioner will look for irritation, injury, inflammation, limited mobility or range of motion due to pain, abnormalities in the strength and sensation of particular parts of the body, further neurologic and radiologic examinations (e.g., MRI, CT, CT myelography, etc.) to explain the persistent pain symptoms the patient experiences. Such pain can exhibit as, for example, radiating pain, weakness, or numbness in the legs, back, arms, or neck. This will allow the practitioner to identify additional suspected pain generators. In this way the practitioner can use the ultrasonic devices and methods to selectively narrow in on the pain generator (e.g., pain generators in nerve areas, facet joints, medial branch nerves, sacroiliac joints, discs) and rule out selective areas where the pain generator is not located. When the patient experiences pain at the site where the ultrasound is applied and the pain generator identified, this will allow the practitioner to diagnose the location of the pain generator. A surgical procedure can now be scheduled to provide long-term relief at the site of the pain generator. In this way, operating on the wrong area and/or suspected pain generator is avoided.

In some embodiments, the patient can be monitored for pain. This can be accomplished by the patient themselves or by the practitioner. As or after the ultrasonic energy is applied, the pain symptoms can be monitored for severity or intensity of pain, reduced disability or increased mobility, alleviation of one or more symptoms associated with the pain, reduced resting pain, shortened duration of pain symptoms, reduced pain sensitivity or sensation in a given time frame. This can alert the practitioner that he/she has successfully found a pain generator.

In some embodiments, the devices and methods described herein are utilized to detect pain generators for vertebral abnormalities, such as, compression fractures, pars defects, vertebral instability, soft tissue abnormalities in ligaments, tendons, annulus, muscles, cartilaginous structures, joints (e.g., facet joints, intervertebral discs, sacroiliac joints, etc.) or abnormalities resulting from tumors, infection or other infiltrative processes. Pain generators resulting from nerve root lesions (e.g., compressive lesions from adjacent discs, hypertrophic facet joints, facet joints cysts, faulty hardware positioning, bony foraminal encroachment, spondylolisthesis, spondylolysis, congenitally short pedicles, nerve sheath tumors, granulation tissue and/or arachnoiditis, etc.), spinal nerve compression (e.g., spinal stenosis), peripheral nerve lesions, femoral neuropathy, meralgia paresthetica, peroneal neuropathy, asymmetrical neuropathies, lower limb joint pathology, vascular pathology, degenerative disc and joint disease or the like.

In some embodiments, the methods and devices herein can be used to diagnose the cause of back pain. For example, in degenerative disc disease, the disc is damaged and by moving the probe closer to the damaged disc, the pain signal can be reproduced at lower ultrasonic frequencies as the pain will be felt by the patient at lower ultrasonic frequencies as the probe directly or indirectly (e.g., through coupling media like fluid) contacts the sensitive damaged tissue.

In some embodiments, the ultrasound energy may be applied to the pain generator or suspected pain generator at a first dosage level sufficient to stimulate the pain generator or suspected pain generator by vibrating the tissue. The ultrasonic energy can be applied as a continuous wave of ultrasound energy from the ultrasound transducer, starting at a zero or quiescent amplitude, and slowly increasing the amplitude until a pain response is noted. Alternatively, the ultrasound energy can be applied in pulse dosing. The pain signal can be verified, for example, by having the patient in a conscious or semi-conscious state and asking the patient when the stimulation from the ultrasonic energy is felt, and asking the patient if the stimulation is at the same location as the pain. In another embodiment, a measurement of neural activity corresponding to the pain may be performed, or a measurement of an electrophysiological signal associated with the pain may be performed to measure the pain signal.

In some embodiments, after the pain generators are isolated and the locations are mapped, treatments of the area can be performed. In this way, the location of the pain generator can be confirmed and the practitioner will know that he/she is operating at the right location. For example, the practitioner now knows the pain generator is between lumbar vertebrae L3 (lumbar 3) and L4 (lumbar 4), and can operate on these levels instead of the wrong level (e.g., L1 and L2).

In some embodiments, the methods and devices described herein can be used with implantable drug depots. For example, a drug depot can be implanted at or near the pain generator and can release a pain reliever or anti-inflammatory agent over a period of about 2 weeks to about 4 weeks or from about 3 days to 4 weeks to reduce the pain.

In some embodiments, a method is provided for diagnosing a pain generator at or near the spine in a patient suffering from pain, the method comprising: positioning an ultrasonic probe at a target tissue site at or near the spine, the ultrasonic probe having a proximal end, a distal end and a longitudinal axis therebetween, the ultrasonic probe supplied with ultrasonic energy from an ultrasonic energy source that transfers ultrasonic energy from a transducer to the proximal end of the ultrasonic probe along the longitudinal axis to the distal end of the ultrasonic probe; delivering a first dose of ultrasonic energy from the distal end of the ultrasonic probe to the target tissue site at or near the spine to produce a first pain signal; re-positioning the ultrasonic probe at a second target tissue site at or near the spine; delivering a second dose of ultrasonic energy from the distal end of the ultrasonic probe to the second target tissue site at or near the spine to produce a second pain signal; and comparing the first dose and the first pain signal to the second dose and the second pain signal to diagnose the pain generator or suspected pain generator, wherein a greater pain signal indicates the presence of the pain generator.

Back Pain

Back pain is a very difficult pain for practitioners throughout the world to treat. The reason often is inadequate diagnosis, or failure to identify the true pain generator. By using the ultrasonic device and methods provided herein, proper diagnosis of the location of the pain generator can be made. Thus the practitioner can identify the pain generator causing the back pain. For example, lumbar spine pain falls into two general categories: purely axial, and radicular or radiating. In patients with purely midline or lateralizing low-back pain, common and uncommon etiologies should be considered. These include pain originating from osseous structures (vertebral compression fractures, pars defects, or vertebral instability), soft tissue (ligaments, tendons, muscles and cartilaginous structures), joints (facet joints, intervertebral discs, sacroiliac joints) as well as tumors, infection or other infiltrative processes. In patients with radicular pain, nerve root lesions (compressive lesions from adjacent discs, hypertrophic facet joints, facet joints cysts, faulty hardware positioning, bony foraminal encroachment caused by spondylolisthesis or spondylolysis, congenitally short pedicles, nerve sheath tumors, granulation tissue and arachnoiditis), spinal nerve compression and peripheral nerve lesions should be considered. By mapping the pain generators and non-pain generators using the ultrasonic devices and methods provided herein, a more definitive diagnosis can be made as to the cause of the pain in the above conditions.

In some embodiments, the ultrasonic devices and methods can be used to confirm diagnosis that does not originate from the spines but is often misdiagnosed (often as classified as referred pain) such as, for example, femoral neuropathy, meralgia paresthetica, peroneal neuropathy, asymmetrical neuropathies, lower limb joint pathology or vascular pathology. These conditions are often mistaken for radicular pain in patients with and without radiographic evidence of degenerative disc and joint disease. Using the diagnostic ultrasonic device and methods of the present application, these conditions now can be more definitively diagnosed.

In some embodiments, the back pain can be caused by a herniated disc. Typically, when a patient has a herniated disc, the patient will exhibit severe or persistent radicular pain. When the herniated disc is in the lower back, persistent pain can originate in the back and often extends ("radiates") into the leg along the distribution of the sciatic nerve (lumbar radicular pain, or sciatica). In patients with herniated disc in the neck, the persistent pain can originate in the neck and often radiates into the arm. Patients can be diagnosed with herniated disc through a variety of characteristic findings. These include, for example: persistent radiating pain; characteristic findings on a physical exam indicative of nerve root irritation, injury or inflammation, such as limited mobility or range of motion due to pain; abnormalities in the strength and sensation of particular parts of the body that are found with a neurological examination, radiologic examination suggestive of a herniated disc. The ultrasonic devices and methods of the present application can assist the practitioner in confirming the location of the pain generator—in this case the herniated disc. Subsequently, a surgery can be performed and partial removal of the nucleus pulposus or annulus fibrosus can be performed. The ultrasonic devices and methods will guide the practitioner and he/she will now know that the right location is being operated on.

Spinal stenosis is another condition where the patient will exhibit, among other things, back pain. Spinal stenosis, either acquired or congenital, results from degenerative changes in the spine, variably including the intervertebral disks, the intervertebral joints (facet joints) and the ligamentum flavum.

In each case, the degenerative changes together result in a gradual narrowing of the lumbar or cervical spinal canal, causing compression of the spinal cord and spinal nerve roots. Symptoms include: pain and/or numbness in the neck, back, buttocks, legs, thighs or calves that is worse with walking, standing and/or exercise; back pain that radiates to the legs; weakness of the legs; and difficulty or imbalance when walking. Patients can be diagnosed with spinal stenosis through, for example, persistent radiating pain; neurologic examination findings of abnormal sensation and muscle weakness in the legs; gait disturbances and characteristic bent over posture; asymmetric deep tendon reflexes; and radiologic findings of spinal stenosis by x-ray (e.g., myelogram), MRI, spinal CT or CT myelography or the like. Depending on whether the stenosis is central or foraminal, provocative maneuvers on physical examination such as side bending reproducing the pain may be negative or positive, respectively. In some embodiments, the ultrasonic devices and methods may be used to diagnose the pain generators for the facet degeneration.

The ultrasonic devices and methods of the present application can assist the practitioner in confirming the location of the pain generator—in this case the abnormality causing the spinal stenosis. Subsequently, a surgery can be performed to treat the spinal stenosis. The practitioner will now know that the right location is being operated on and long term pain relief can be provided to the patient.

In some embodiments, ultrasonic devices and methods of the present application can be used to triangulate the pain generators. Thus, a plurality of probes (at least two, at least three, at least four, at least five, at least six, at least seven, etc.) can be placed around the target tissue site (also known as the pain generator or pain generation site) such that the target tissue site falls within a region that is either between the probes when there are two, or within an area whose perimeter is defined by a set of plurality of probes.

Although the spinal site is shown in FIGS. 3 and 4, as described above, the ultrasonic probe and thus the ultrasound can be delivered to any site beneath the skin, including, but not limited to, at least one muscle, ligament, tendon, cartilage, spinal disc, spinal foraminal space, near the spinal nerve root, or spinal canal.

Kits

In various embodiments, the ultrasonic device is packaged in a kit housing one or more ultrasonic probes, leads and monitoring equipment. The kit may include additional parts along with the ultrasonic device, for example, disposable probe tips, cannulas, drug depots and/or medical device combined together to be used detect one or more pain generators. The kit may include the ultrasonic probe in one compartment and the ultrasonic energy device in a second compartment. The third compartment may include drug depots or each drug depot with a different release profile may be labeled and placed in a different compartment (e.g., bolus dose depot compartment, sustained release depot compartment, etc.) and any other instruments needed for the localized drug delivery. A third compartment may include gloves, drapes, wound dressings and other procedural supplies for maintaining sterility, as well as an instruction booklet and a DVD showing how the device operates. A fourth compartment may include additional cannulas and/or needles. Each tool may be separately packaged in a plastic pouch that is radiation sterilized. A fifth compartment may include an agent for radiographic imaging. A cover of the kit may include illustrations of the ultrasonic probe procedure and a clear plastic cover may be placed over the compartments to maintain sterility.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A method for diagnosing a pain generator at or near the spine in a patient suffering from pain, the method comprising:
positioning an ultrasonic probe at a target tissue site at or near the spine, the ultrasonic probe having a proximal end, a distal end and a longitudinal axis therebetween, wherein the distal end of the probe defines a blunt tip configured to penetrate the skin of the patient and comprises at least one orifice configured to deliver a coupling medium at the target tissue site and the proximal end is configured to remain outside the body of a patient, wherein the ultrasonic probe has a changing diameter from its proximal end to its distal end, the ultrasonic probe having a needle configured to penetrate skin, the needle having a channel therethrough configured to receive the proximal end and distal end of the ultrasonic probe, at least the distal end of the ultrasonic probe is retractable within the channel of the needle or extendible from the channel of the needle, and the distal end of the probe includes at least one LED sensor for tracking a position and direction of the probe, the LED sensor configured for positioning at or near a spinal disc or facet, the ultrasonic probe supplied with ultrasonic energy having a high frequency in the approximate range of 0.7 MHz-3 MHz or 0.7 MHz-1 MHz from an ultrasonic energy source that transfers ultrasonic energy from a transducer to the proximal end of the ultrasonic probe along the longitudinal axis to the distal end of the ultrasonic probe;
penetrating the skin with the needle;
delivering a first dose of ultrasonic energy from the distal end of the ultrasonic probe to the target tissue site at or near the spine to produce a first pain signal;
re-positioning the ultrasonic probe at a second target tissue site at or near the spine;
delivering a second dose of ultrasonic energy from the distal end of the ultrasonic probe to the second target tissue site at or near the spine to produce a second pain signal; and
comparing the first dose and the first pain signal to the second dose and the second pain signal to diagnose the pain generator or suspected pain generator,
wherein a greater pain signal indicates the presence of the pain generator, and the first dose and the second dose are the same dose and the ultrasonic probe and needle are bent.

2. A method for diagnosing a pain generator according to claim 1, wherein the ultrasonic probe is re-positioned at a suspected pain generator a plurality of times before it is positioned at a pain generator, so that the location of the pain generator is diagnosed.

3. A method for diagnosing a pain generator according to claim 1, wherein the ultrasonic probe is re-positioned at a plurality of suspected pain generators before it is re-positioned at a plurality of pain generators so that the location of the pain generators can be mapped.

4. A method for diagnosing a pain generator according to claim 1, wherein the ultrasonic probe has a diameter of about 14 gauge to 25 gauge.

5. A method for diagnosing a pain generator according to claim 1, wherein (i) the positioning and re-positioning of the ultrasonic probe is performed using radiography, fluoroscopy, luminescence, positron emission tomography (PET), single photon emission computed tomography (SPECT), CT, MRI, and/or X-ray imaging techniques to triangulate one or more pain generators; (ii) the positioning and re-positioning of the ultrasonic probe is performed to map one or more pain generators; or (iii) one or more ultrasonic probes are used.

* * * * *